United States Patent
Aykroyd et al.

(10) Patent No.: US 9,097,720 B2
(45) Date of Patent: Aug. 4, 2015

(54) DISPLAYING GLUCOSE MEASUREMENTS ON A HANDHELD GLUCOSE METER

(71) Applicant: Roche Diagnostics Operations, Inc., Indianapolis, IN (US)

(72) Inventors: Timothy N. Aykroyd, Carmel, IN (US); Stacia R. Davis, Indianapolis, IN (US); Erin K. McKinney, Brownsburg, IN (US); Mark G. Mears, Westfield, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/031,106

(22) Filed: Sep. 19, 2013

(65) Prior Publication Data
US 2015/0079689 A1   Mar. 19, 2015

(51) Int. Cl.
*G01N 33/66* (2006.01)
*G01N 33/48* (2006.01)

(52) U.S. Cl.
CPC ................ *G01N 33/66* (2013.01); *G01N 33/48* (2013.01)

(58) Field of Classification Search
CPC ............................... G01N 33/48; G01N 33/66
USPC ........... 436/63, 95; 435/14; 702/19; 422/68.1
See application file for complete search history.

(56) References Cited

U.S. PATENT DOCUMENTS

| | | | | |
|---|---|---|---|---|
| 4,731,726 | A * | 3/1988 | Allen, III | 600/300 |
| 7,976,467 | B2 * | 7/2011 | Young et al. | 600/365 |
| 2007/0176867 | A1 * | 8/2007 | Reggiardo et al. | 345/87 |
| 2010/0331650 | A1 * | 12/2010 | Batman et al. | 600/365 |
| 2011/0034786 | A1 * | 2/2011 | Cadio et al. | 600/316 |
| 2011/0124996 | A1 | 5/2011 | Reinke et al. | |
| 2012/0232520 | A1 * | 9/2012 | Sloan et al. | 604/504 |
| 2013/0172706 | A1 * | 7/2013 | Carlsgaard et al. | 600/365 |
| 2013/0172710 | A1 * | 7/2013 | Mears et al. | 600/365 |

* cited by examiner

*Primary Examiner* — Maureen Wallenhorst
(74) *Attorney, Agent, or Firm* — Harness, Dickey

(57) ABSTRACT

A computer-implemented method is provided for displaying glucose measurements of a person on a handheld glucose meter. The method includes: determining a current blood glucose measurement for a person from a test strip inserted into a port of the handheld glucose meter; displaying the current glucose measurement on a result screen of the handheld glucose meter immediately following the measurement of the current glucose measurement by the handheld glucose meter; providing an indicium of a logbook screen on the result screen concurrently with the display of the current glucose measurement on the result screen; and displaying the logbook screen in response to a user input received by the handheld glucose meter, where the logbook screen displays the current glucose measurement along with at least two preceding glucose measurements of the person.

20 Claims, 8 Drawing Sheets

DISPLAYING GLUCOSE MEASUREMENTS ON A HANDHELD GLUCOSE METER

FIELD

The present disclosure relates generally to medical devices and more particularly to a system and method for displaying glucose measurements of a person on a handheld glucose meter.

BACKGROUND

Persons with diabetes have difficulty regulating blood glucose levels in their bodies. As a consequence, many of these persons carry specialized electronic meters, called blood glucose meters, which allow them to periodically measure their glucose levels and take appropriate action, such as administering insulin. After measuring their current glucose level, some persons may want to view a logbook that displays a history of their preceding glucose levels. Some persons may want to view the logbook to see changes in their glucose levels, for example. Therefore, there is a need for a glucose meter that allows a user to review the logbook after taking a blood glucose measurement.

This section provides background information related to the present disclosure which is not necessarily prior art.

SUMMARY

In one aspect of this disclosure, a computer-implemented method is provided for displaying glucose measurements of a person on a handheld glucose meter. The computer-implemented method includes: determining, by the handheld glucose meter, a current blood glucose measurement for a person from a test strip inserted into a port of the handheld glucose meter, the test strip having a reaction site for receiving a sample of fluid from a patient; displaying, by the handheld glucose meter, the current glucose measurement on a result screen of the handheld glucose meter immediately following the measurement of the current glucose measurement by the handheld glucose meter; providing, by the handheld glucose meter, an indicium of a logbook screen on the result screen concurrently with the display of the current glucose measurement on the result screen; and displaying, by the handheld glucose meter, the logbook screen in response to a user input received by the handheld glucose meter, where the logbook screen displays the current glucose measurement along with at least two preceding glucose measurements of the person.

In another aspect of this disclosure, a handheld glucose meter is presented. The handheld glucose meter includes: a display; a port configured to receive a test strip having a reaction site for receiving a sample of blood from a patient; a glucose measurement module that operates to determine a current blood glucose measurement for a patient from a test strip inserted into the port of the handheld glucose meter; and a user interface module in data communication with the glucose measurement module and the display. The user interface module operates to display the current glucose measurement on a result screen of the display in response to the measurement of the current glucose measurement by the glucose measurement module; provide, on the display, an indicium of a logbook screen on the result screen concurrently with the display of the current glucose measurement on the result screen; receive a user input to display the logbook screen; and display the logbook screen in response to the user input received by the handheld glucose meter, where the logbook screen displays the current glucose measurement along with at least two preceding glucose measurements of the patient.

In yet another aspect of this disclosure, a computer-implemented method is provided for displaying blood glucose measurements of a patient on a handheld blood glucose meter. The computer-implemented method includes: determining, by the handheld blood glucose meter, a current blood glucose measurement for the patient from a test strip inserted into a port of the handheld blood glucose meter, the test strip having a reaction site for receiving a sample of blood from the patient; displaying, by the handheld blood glucose meter, the current blood glucose measurement on a result screen of the handheld blood glucose meter in response to the measurement of the current blood glucose measurement by the handheld blood glucose meter; displaying, by the handheld blood glucose meter, a single previous blood glucose measurement of the patient on the result screen concurrently with the display of the current blood glucose measurement on the result screen; receiving, by the handheld blood glucose meter, a selection of the single previous blood glucose measurement being displayed on the result screen; and displaying, by the handheld blood glucose meter, a logbook screen in response to the selection received by the handheld blood glucose meter, where the logbook screen displays the current blood glucose measurement along with at least two previous glucose measurements of the patient.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present

DETAILED DESCRIPTION

Figure 1:
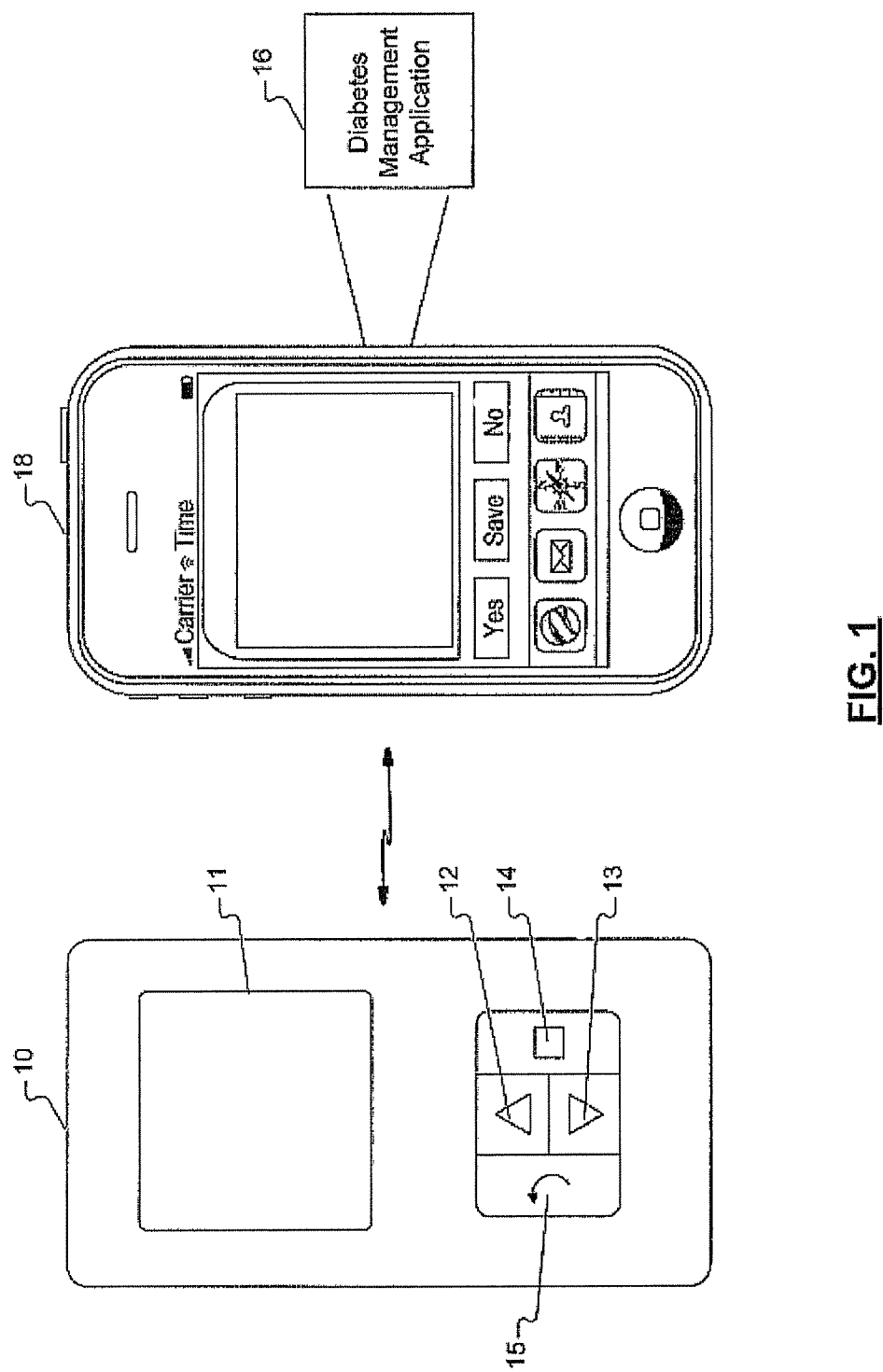
FIG. 1 is a diagram depicting a handheld glucose meter in data communication with a diabetes management application residing on a mobile phone.

FIG. 1 depicts an example handheld glucose meter 10. The handheld glucose meter 10 includes a display 11 and various buttons that can be a user to control the handheld glucose meter 10. The buttons may include an up button 12, a down button 13, a select button 14 and a back button 15. The up button 12 and the down button 13 may be used to scroll up and down a screen being displayed on the display 11. The select button 14 may be used to make a selection, such as to press 'OK' or to click on an option being displayed on the display 11. The back button 15 may be used to navigate back to a previous screen being displayed on the handheld glucose meter 10.

In this example embodiment, the handheld glucose meter 10 is in data communication via a wireless data link with a diabetes management application 16. The handheld glucose meter 10 is configured to receive a sample of blood from a patient and determine a blood glucose measure for the patient from the blood sample. One or more blood glucose measurements may in turn be transmitted over the wireless data link to the diabetes management application 16 for further processing. In an example embodiment, the diabetes management application 16 resides on a mobile phone 18. In other embodiments, the diabetes management application 16 may be native to a remote server with its user interface presented on the mobile phone 18. In some embodiments, data is transferred to and from the handheld glucose meter 10 using the Bluetooth wireless technology standard (e.g., low energy feature of Bluetooth 4.0) although other types of communication transports are contemplated by this disclosure, such as Wi-Fi, ZigBee, NFC (Near Field Communications), or the like.

Figure 2:
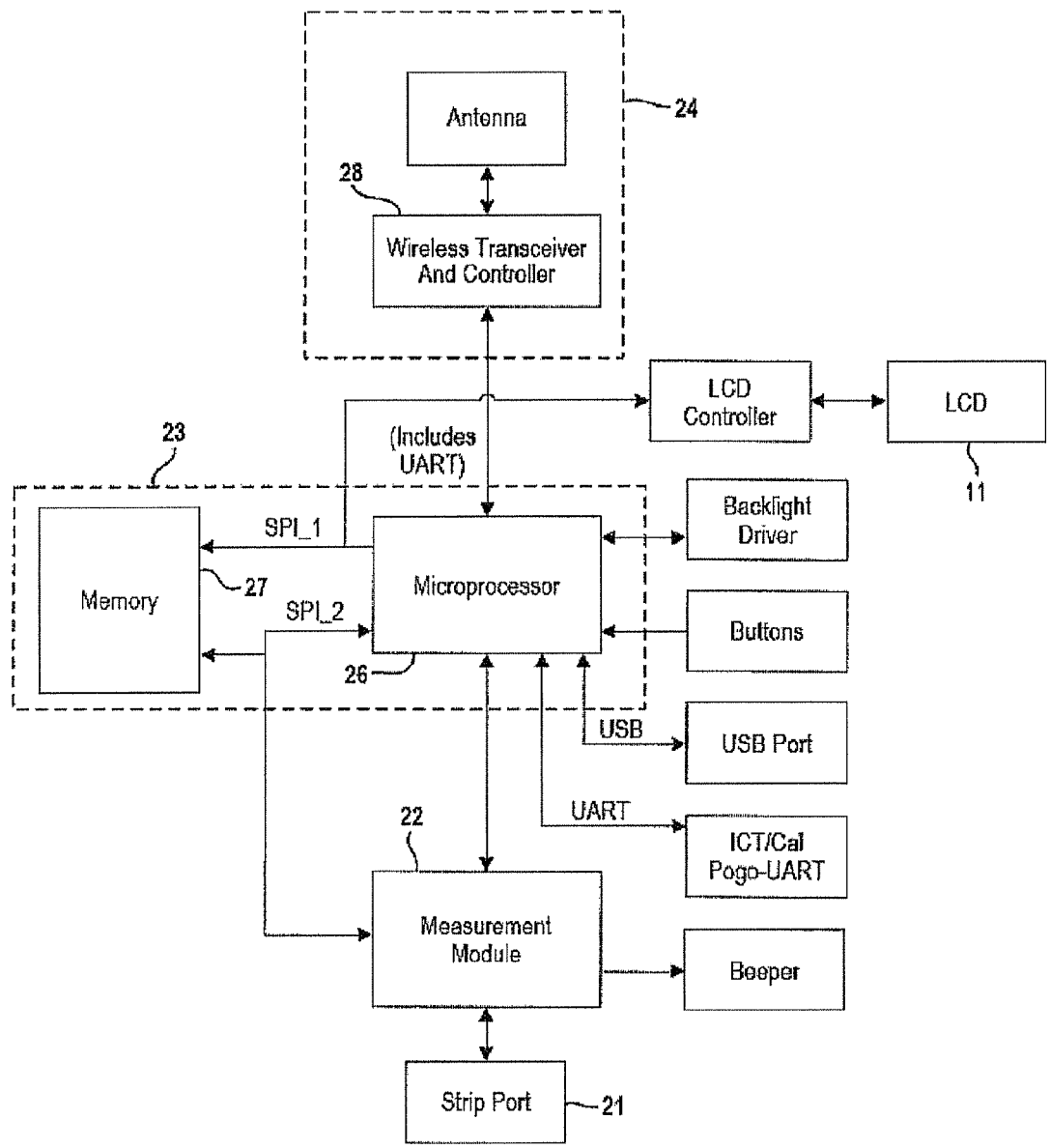
FIG. 2 is a block diagram of an example hardware arrangement for the handheld glucose meter.

FIG. 2 depicts an example hardware arrangement for the handheld glucose meter 10. The handheld glucose meter 10 is comprised generally of a measurement module 22, a processing subsystem 23 and a communication subsystem 24. Each of these components is further described below. While the primary components are discussed herein, it is understood that other components (e.g., batteries) may be needed for the overall operational of the meter.

The measurement module 22 cooperatively interacts with a test strip inserted into a strip port 21 to determine a glucose measurement from the sample of blood on the test strip. The measurement module 22 may include a code key that includes calibration information for the test strips being read by the meter. As used herein, the term module may refer to, be part of, or include an application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above. The term module may further include memory that stores code executed by the processor, where code, as used above, may include software, firmware, and/or microcode, and may refer to programs, routines, functions, classes, and/or objects.

The processing subsystem 23 is configured to receive the glucose measurements from the measurement module 22 which may in turn be stored by the processing subsystem 23. Glucose measurements may also be displayed by the processing subsystem 23 on the display 11. The user can interact with the meter using various user interface components, such as buttons (e.g. the buttons 12, 13, 14, 15), switches, a speaker, a microphone, USB port, etc. Each of these components is interfaced with the processing subsystem 23. In an exemplary embodiment, the processing subsystem 23 includes a microprocessor 26 and one or more volatile and/or non-volatile memories 27 although other implementations are envisioned for the processing subsystem.

The processing subsystem 23 is also interfaced with the communication subsystem 24. In an exemplary embodiment, the communication module includes a wireless transceiver 28. The wireless transceiver operates to communicate the glucose measurements and other data wirelessly via a data link to a remote device physically separated from the meter. The communication subsystem can also include an antenna, microcontroller, voltage and power control circuits and a flash memory device. Although a few primary components of the handheld glucose meter 10 are discussed herein, it is readily understood that other components (e.g., power source) may be needed to implement the meter.

Figure 3:
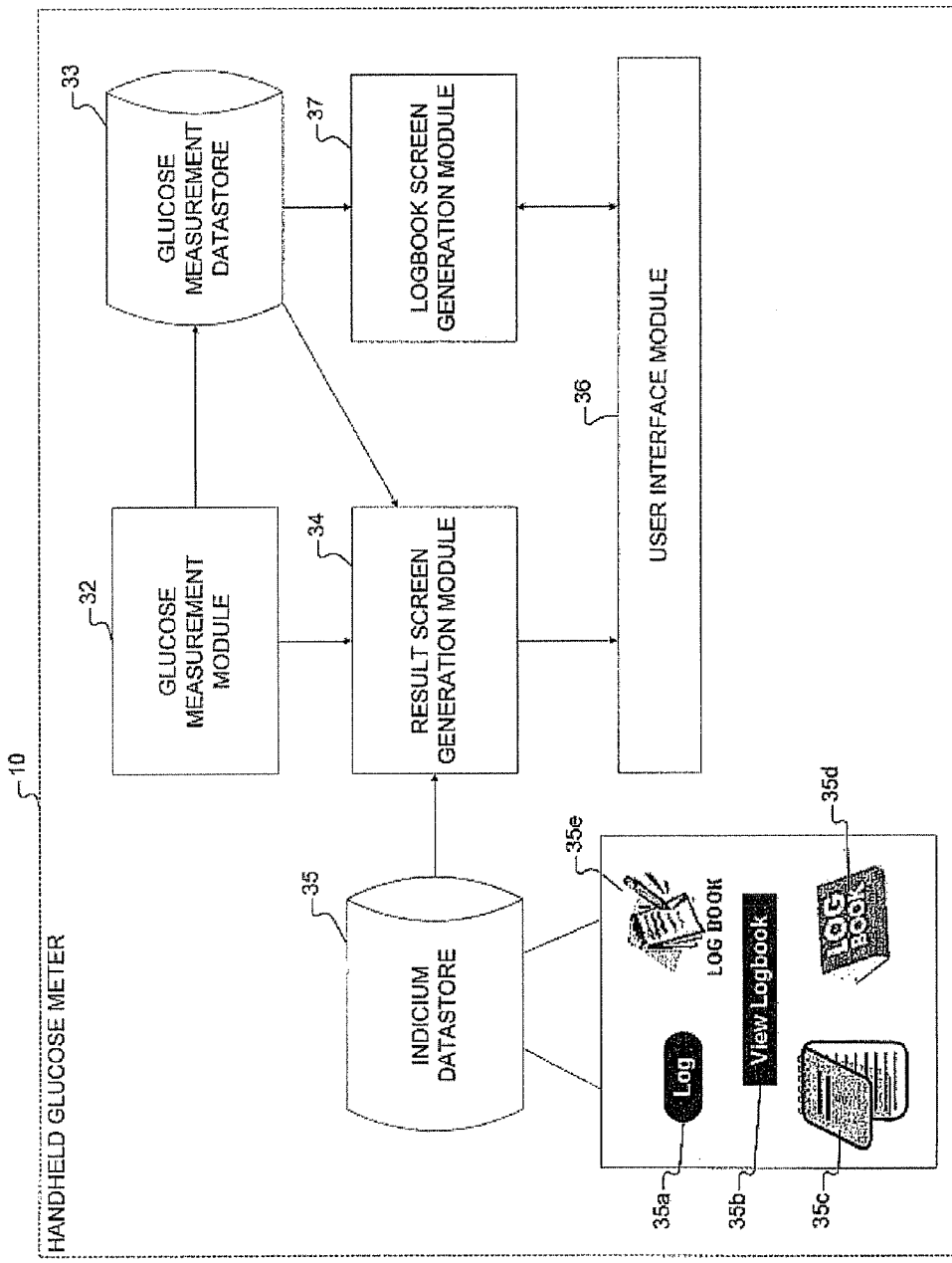
FIG. 3 is a block diagram illustrating an example handheld glucose meter.

FIG. 3 depicts an example embodiment of the handheld glucose meter 10. In this example embodiment, the handheld glucose meter 10 includes a glucose measurement module 32, a glucose measurement datastore 33, a result screen generation module 34, an indicium datastore 35, a user interface module 36 and a logbook screen generation module 37.

The glucose measurement module 32 is similar to the measurement module 22. The glucose measurement module 32 determines a current blood glucose measurement for a person, for example based on a test strip inserted into the strip port 21 as described above. The glucose measurement module 32 may store the current blood glucose measurement in the glucose measurement datastore 33. The glucose measurement datastore 33 may reside in the memory 27. The glucose measurement module 32 may send the current blood glucose measurement to the result screen generation module 34.

Figure 5:
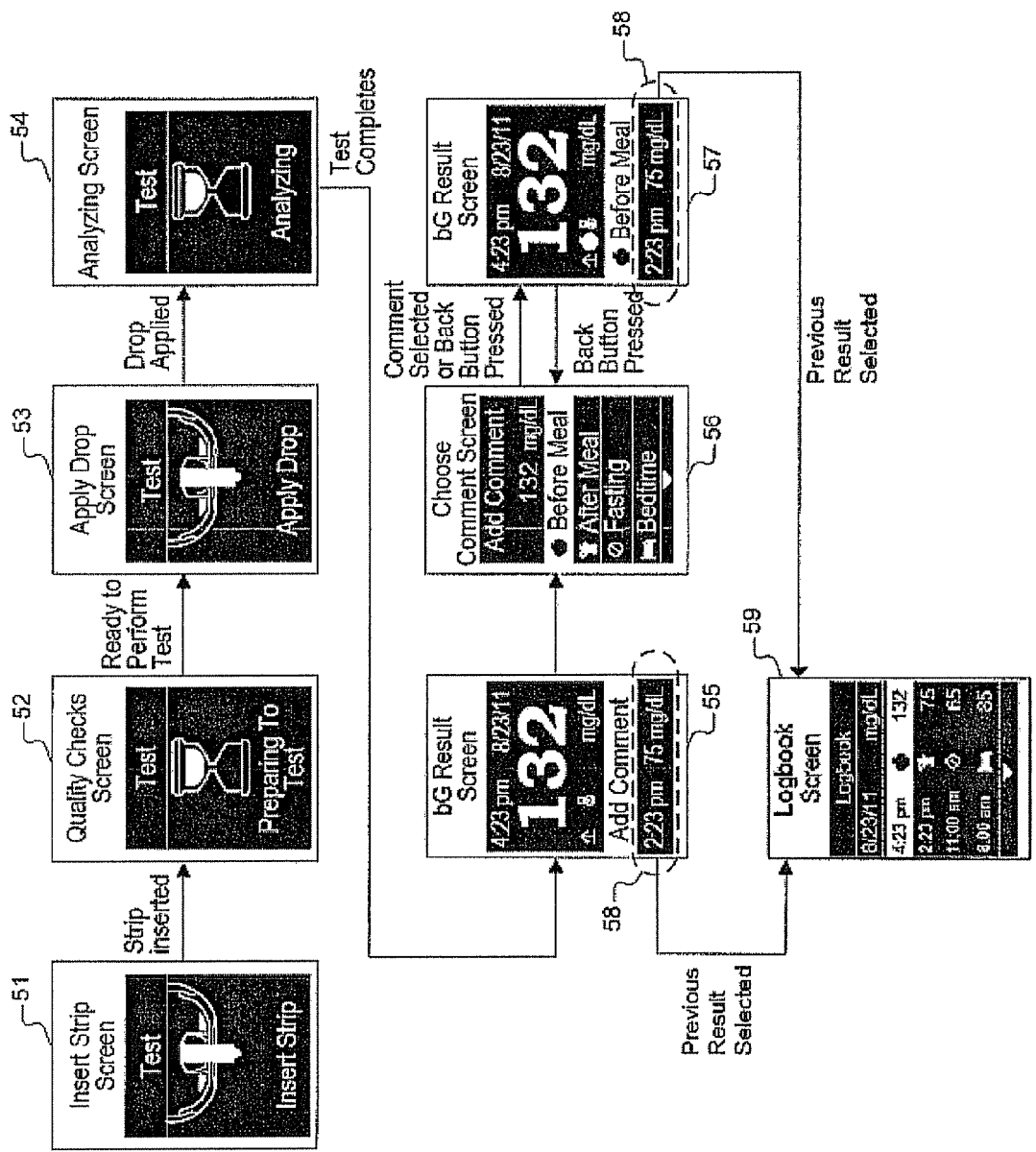
FIG. 5 depicts example screens displayed on the handheld glucose meter during a testing scenario.

The result screen generation module 34 generates a result screen (e.g. result screen 55 shown in FIG. 5). The result screen includes the current blood glucose measurement. The result screen generation module 34 may receive the current blood glucose measurement from the glucose measurement module 32. Alternatively, the result screen generation module 34 may retrieve the current blood glucose measurement from the glucose measurement datastore 33.

In addition to the current blood glucose measurement, the result screen may include an indicium for a logbook screen. In this example embodiment, the indicium for the logbook screen is a single preceding blood glucose measurement (e.g. indicium 58 shown in FIG. 5). The result screen generation module 34 may retrieve the single preceding blood glucose measurement from the glucose measurement datastore 33.

In another example embodiment, the result screen generation module 34 may retrieve the indicium for the logbook screen from the indicium datastore 35. The indicium datastore 35 may include indicia 35a-e that may include icons, labels or images that can be used to represent a logbook. The result screen generation module 34 may retrieve one of the indicia from the indicium datastore 35 and include the retrieved indicium in the result screen (e.g. indicium 58' shown in FIG. 6B). In this example embodiment, the result screen may include the indicium for the logbook screen and only the current blood glucose measurement, not any preceding blood glucose measurements (e.g. result screen 55' shown in FIG. 6B).

Figure 6A:
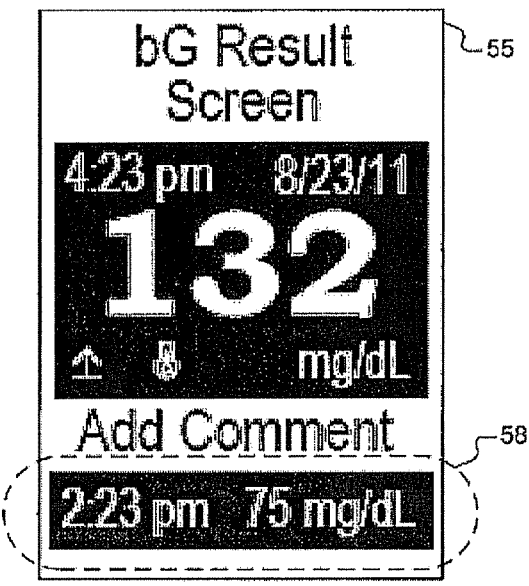
FIG. 6A is a diagram that illustrates an example result screen displayed on the handheld glucose meter.
Figure 6B:
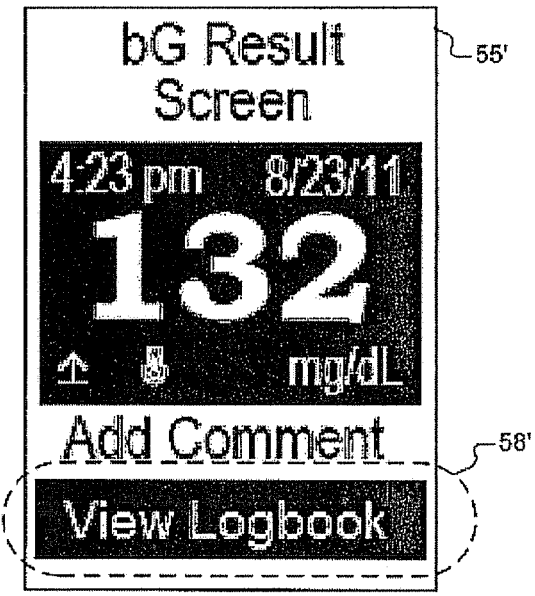
FIG. 6B is a diagram that illustrates another example result screen displayed on the handheld glucose meter.
Figure 6C:
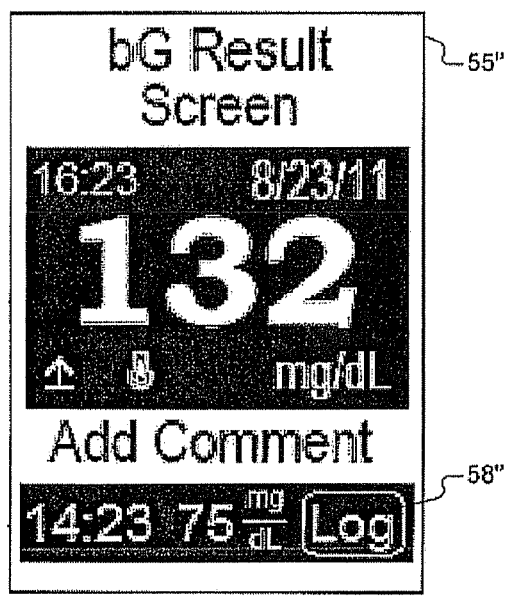
FIG. 6C is a diagram that illustrates yet another example result screen displayed on the handheld glucose meter.

In yet another example embodiment, the result screen may include the current blood glucose measurement, the single preceding blood glucose measurement and an indicium for the logbook screen that may be selected from the indicium datastore 35 (e.g. indicium 58" shown in FIG. 6C). The indicium for the logbook screen may be separate from the single preceding blood glucose measurement. In this example embodiment, the result screen may include the indicium for the logbook screen, the current blood glucose measurement and a single preceding blood glucose measurement, not other preceding blood glucose measurements (e.g. result screen 55" shown in FIG. 6C).

Upon generating the result screen, the result screen generation module 34 may cooperate with the user interface module 36 to display the result screen on the display 11 of the handheld glucose meter 10. The user interface module 36 displays the result screen generated by the result screen generation module 34 on the display 11 of the handheld glucose meter 10. The result screen includes the current blood glucose measurement and the indicium for the logbook screen. As described above, the indicium for the logbook screen may be the single preceding blood glucose measurement or an indicium that is selected from the indicium datastore 35.

When the result screen is being displayed on the display 11, the user interface module 36 may receive a user input to display the logbook screen. The user input to display the logbook screen may be received via the buttons 12, 13, 14 and 15. In this example embodiment, the user input to display the logbook screen may be received when a user selects the indicium for the logbook screen that is displayed on the result screen. The user may select the indicium for the logbook screen by depressing the select button 14. If the indicium for the logbook screen is the single preceding blood glucose measurement, then the user input to display the logbook screen may be received when the user selects the single preceding blood glucose measurement. If the indicium for the logbook screen is an icon, an image or a label selected from the indicium datastore 35, then the user input to display the logbook screen may be received when the user selects the icon, the image or the label being displayed on the result screen.

The user interface module 36 invokes the logbook screen generation module 37 in response to receiving the user input to display the logbook screen. The logbook screen generation module 37 generates a logbook screen (e.g. logbook screen 59 shown in FIG. 5). The logbook screen includes a plurality of preceding blood glucose measurements. The logbook screen may include the current blood glucose measurement and at least two preceding blood glucose measurements of the person. The logbook screen generation module 37 may retrieve the current blood glucose measurement and the two preceding blood glucose measurements from the glucose measurement datastore 33.

In this example embodiment, the logbook screen generation module 37 retrieves at least two preceding blood glucose measurements from the glucose measurement datastore 33. In another example embodiment, the logbook screen generation module 37 may retrieve all preceding blood glucose measurements or all preceding blood glucose measurements from the same day as the current blood glucose measurement.

The logbook screen generation module 37 may display the current blood glucose measurement in a different manner than the preceding blood glucose measurements. For example, the current blood glucose measurement may be highlighted or annotated, whereas the preceding blood glucose measurements may be left unhighlighted or unannotated. The logbook screen generation module 37 may cooperate with the user interface module 36 to display the logbook screen on the display 11.

The user interface module 36 may provide the user with an option to navigate within the logbook screen. For example, the user interface module 36 may scroll the logbook screen to display earlier blood glucose measurements in response to the user pressing the down button 13 on the handheld glucose meter 10. The user interface module 36 may navigate away from the logbook screen and back to the result screen in response to the user pressing the back button 15 on the handheld glucose meter 10.

Figure 4:
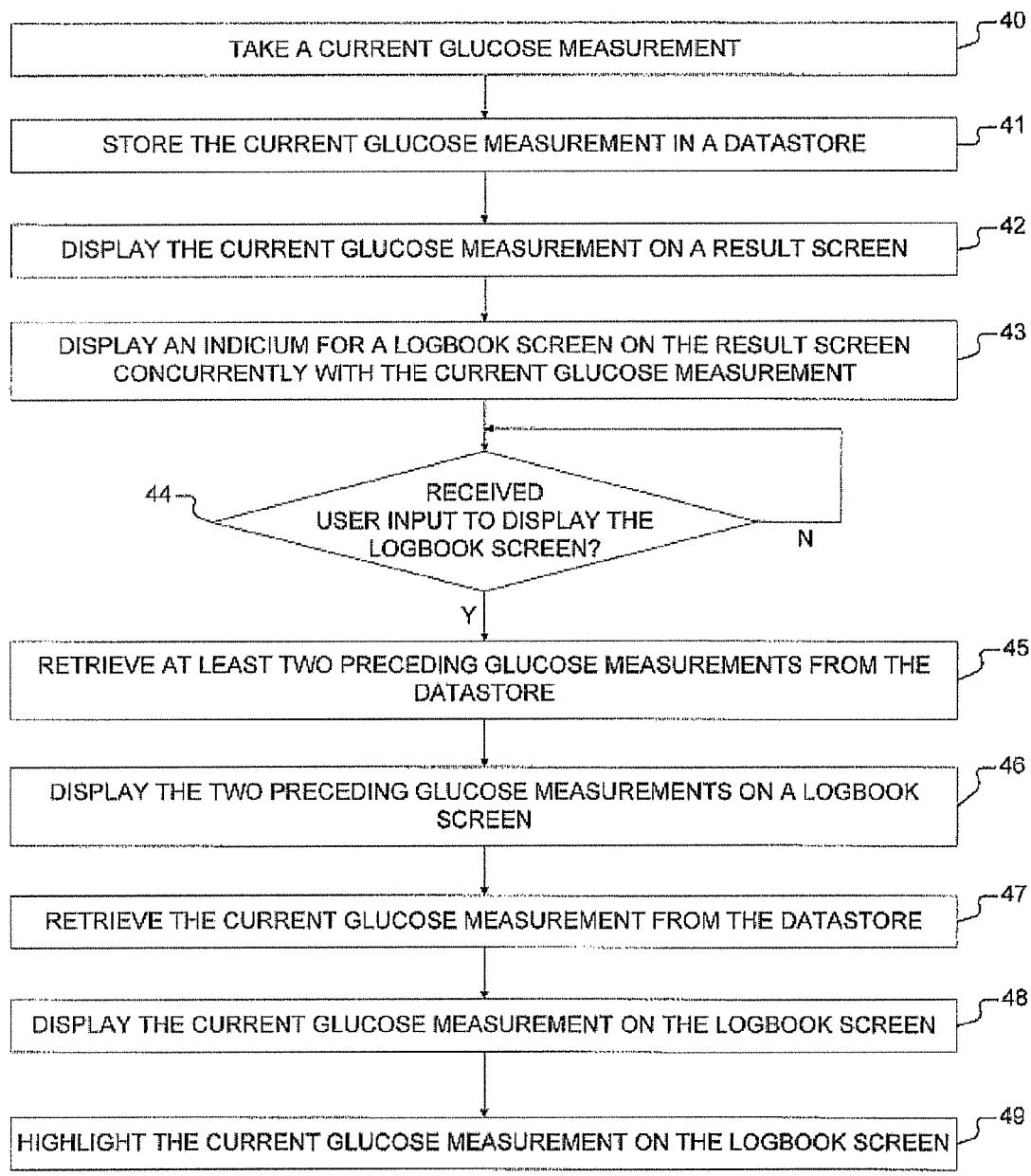
FIG. 4 is a flow diagram illustrating an example method for displaying glucose measurements of a person.

FIG. 4 depicts an example method for displaying the logbook screen. A current glucose measurement is taken at 40. The current glucose measurement may be taken by the glucose measurement module 32 as described above. The current glucose measurement is stored at 41. The current glucose measurement may be stored in the glucose measurement datastore 33 as described above.

The current glucose measurement is displayed on a result screen at 42. In this example embodiment, the current glucose measurement is displayed on the result screen immediately after the measurement is taken. In other embodiments, a user input may be required to display the current blood glucose measurement.

An indicium for a logbook screen is displayed on the result screen at 43. The indicium for the logbook screen is displayed concurrently with the current blood glucose measurement. As explained above, the indicium for the logbook screen may be a single preceding glucose measurement or the indicium for the logbook screen may be an icon, a label or an image selected from the indicium datastore 35.

If a user input to display the logbook screen is received at 44, then a plurality of preceding blood glucose measurements are retrieved from the datastore and displayed on a logbook screen. For example, at least two preceding glucose measurements are retrieved from the datastore at 45 and displayed on the logbook screen at 46. However, if the database only has a single preceding blood glucose measurement stored therein then the single preceding blood glucose measurement is retrieved. Similarly, if the database has no preceding blood glucose measurements then a message may be displayed on the logbook screen (e.g. 'no previous measurements'). As explained above, the preceding glucose measurements may be retrieved by the logbook screen generation module 37 from the glucose measurement datastore 33.

The current glucose measurement may also be retrieved from the datastore at 47 and displayed on the logbook screen at 48. The current glucose measurement may be highlighted on the logbook screen at 49. In other embodiments, the current glucose measurement is annotated in some other way, for example the current glucose measurement may be displayed in a different font than the preceding glucose measurements.

FIG. 5 illustrates example screens displayed on the handheld glucose meter 10 during a testing scenario. From a main menu screen, the user may elect to perform a glucose test. An insert strip screen 51 may be displayed when the user selects a 'perform test' item on the main menu and a test strip is not inserted into the handheld glucose meter 10. Once a test strip has been inserted, a quality check screen 52 may appear and is displayed while a quality check is performed by the handheld glucose meter 10. The quality check screen 52 may also appear when the user selects the 'perform test' item on the main menu and a test strip is present in the handheld glucose meter 10. Once the quality check has been completed, the handheld glucose meter 10 is ready to perform a test.

To begin a test, the user may be prompted to apply a blood sample by displaying an apply drop screen 53. In response to the prompt, the user provides a blood sample using the test strip, where the test strip includes a reaction site that receives the blood sample from the patient. Upon receipt of the blood sample, the handheld glucose meter 10 proceeds to analyze the blood sample in a manner readily known in the art. An analyzing screen 54 may be displayed while the test is being performed by the handheld glucose meter 10.

Once the test completes, a current blood glucose measurement is displayed on a result screen 55. A numeric value for the current blood glucose measurement is displayed along with other information pertaining to the measurement. Upon seeing the current blood glucose measurement, the user may elect to navigate away from the result screen 55, for example by depressing the back button 15. In this case, the user will return to the main menu screen and the result may be transmitted.

Alternatively, upon seeing the current blood glucose measurement, the user may elect to enter a comment pertaining to the glucose measurement. To do so, the user may use the up button 12 or the down button 13 to select the add comment function on the result screen 55. A choose comment screen 56 may be displayed in response to the user electing to enter a comment. In this example embodiment, the user may select from a listing of comments which include 'before meal', 'after meal', 'fasting' and 'bedtime'. After the user selects a comment from the list, a result screen 57 is displayed. It is noted that the result screen 57 displays the selected comment along with the current blood glucose measurement.

After reviewing the result screen 57, the user may elect to navigate away from the result screen 57. In response to navigating way from the result screen 57, the handheld glucose meter 10 may try transmitting the glucose measurement, including any comment, automatically to a paired device (e.g. the mobile phone 18).

The result screens 55 and 57 display an indicium 58 for a logbook screen. In this example embodiment, the indicium 58 for the logbook screen is a single preceding glucose measurement. As discussed above, in other embodiments, the indicium 58 may be an icon, a label or an image that may be selected from the indicium datastore 35. In this example embodiment, the indicium 58 is the same as the single preceding blood glucose measurement being displayed on the result screens 55 and 57. In other embodiments, the indicium 58 may be separate from the single preceding blood glucose measurement. The user may elect to view the logbook screen by selecting the indicium 58. The user may select the indicium 58 by depressing the select button 14.

In response to receiving a user input to display the logbook screen, a logbook screen 59 is displayed. The logbook screen 59 includes a plurality of blood glucose measurements that were captured by the handheld glucose meter 10 in the past. In this embodiment, the logbook screen 59 includes the current blood glucose measurement and three preceding blood glucose measurements of the person. In other embodiments, the logbook screen 59 may only include two preceding blood glucose measurements of the person. If there is only a single preceding blood glucose measurement, then the logbook screen 59 displays the single preceding blood glucose measurement. If there are no preceding blood glucose measurements, then the logbook screen 59 may display a message indicating that there are no preceding blood glucose measurements (e.g. 'no preceding measurements'). As explained earlier, the logbook screen generation module 37 may retrieve the current blood glucose measurement and the preceding blood glucose measurements from the glucose measurement datastore 33.

FIG. 6A depicts an example result screen 55. The result screen 55 displays data corresponding with a current blood glucose measurement (132 mg/dL). The result screen 55 also displays the indicium 58 for the logbook screen. In this example embodiment, the indicium 58 for the logbook screen is a preceding blood glucose measurement (75 mg/dL).

FIG. 6B depicts another example result screen 55'. The result screen 55' displays data corresponding with a current blood glucose measurement (132 mg/dL). The result screen 55' only displays data corresponding with the current blood glucose measurement and not any preceding blood glucose measurements. The result screen 55' also displays an indicium 58' ('View Logbook') for a logbook screen. The indicium 58' for the logbook may be a label from the indicium datastore 35.

FIG. 6C depicts yet another example result screen 55". The result screen 55" displays data corresponding with the current blood glucose measurement (132 mg/dL) and a single preceding glucose result (75 mg/dL). The result screen 55" also displays an indicium 58" for the logbook screen. The indicium 58" may be an image from the indicium datastore 35.

The indicia 58, 58' and 58" may be selected be a user of the handheld glucose meter 10 to provide a user input to the handheld glucose meter 10 to display the logbook screen. In response to receiving the user input to display the logbook screen, the handheld glucose meter 10 may display the logbook screen 59 shown in FIG. 6D.

Figure 6D:
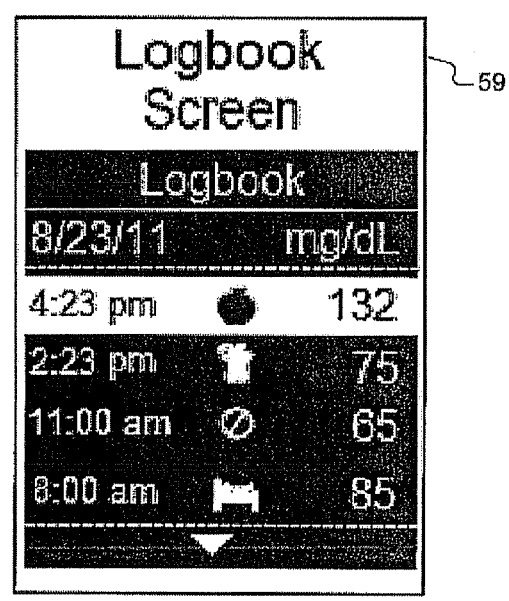
FIG. 6D is a diagram that illustrates an example logbook screen displayed on the handheld glucose meter.

FIG. 6D depicts an example logbook screen 59. The logbook screen 59 displays a current blood glucose measurement (132 mg/dL) and three preceding blood glucose measurements (75 mg/dL, 65 mg/dL and 85 mg/dL). The current blood glucose measurement has been highlighted to indicate that the current blood glucose measurement is the most recent blood glucose measurement.

Figure 7:
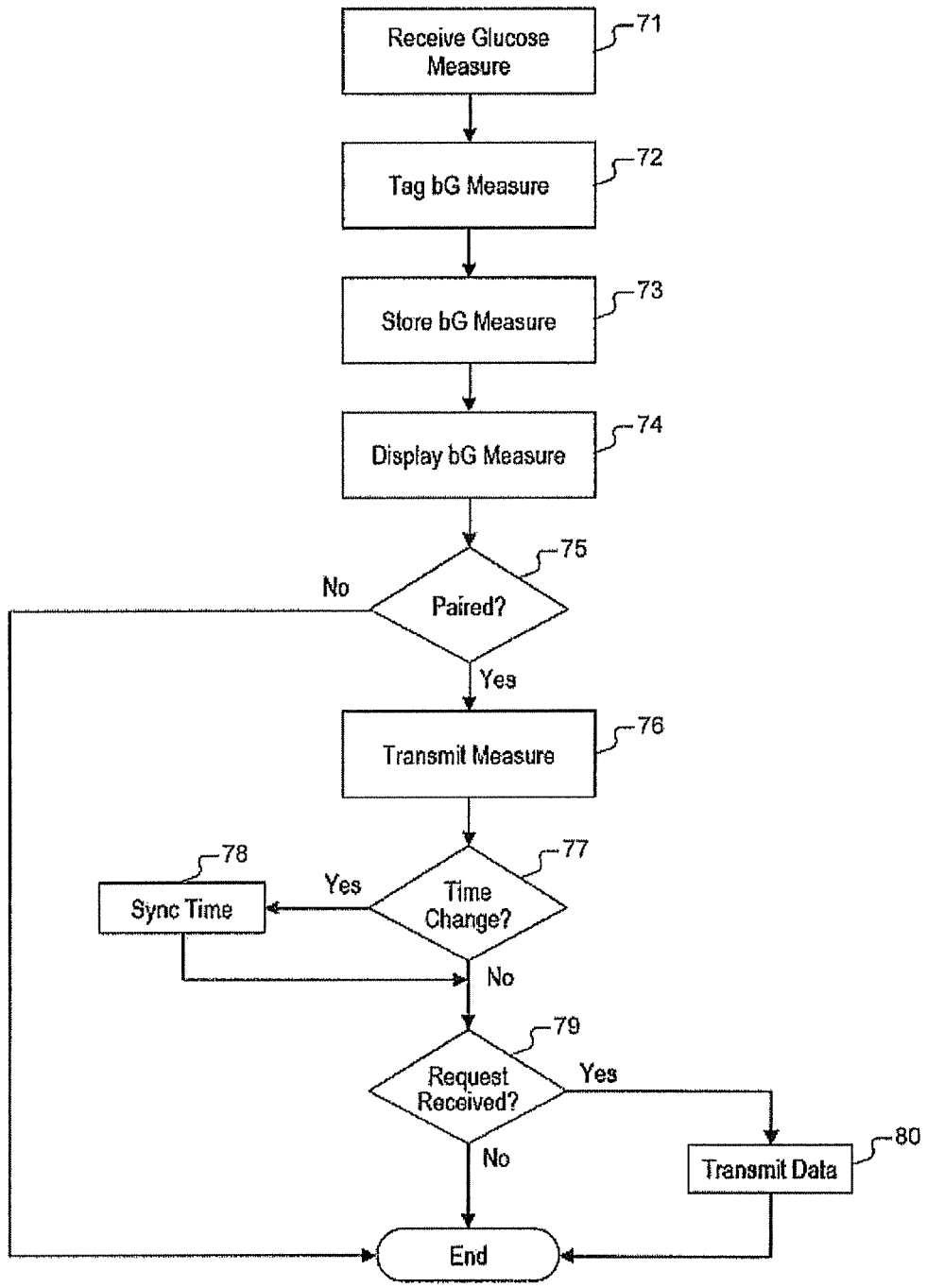
FIG. 7 is a flow diagram illustrating an example technique for transmitting blood glucose measurements individually from the handheld glucose meter.

Rather than sending blood glucose measurements in a batch manner, the handheld glucose meter 10 may be configured to transmit blood glucose measurements individually as shown in FIG. 7. The blood glucose measurements may be transmitted, for example to a mobile phone (e.g. the mobile phone 18) or some other portable computing device carried by the user. Because the mobile phone is typically in close proximity to the user, it may be used as a data collector for the patient's blood glucose measurements. A diabetes management application 16 residing on the mobile phone 18 can then be used for data analysis as well as other sophisticated diabetes management functions. Consequently, the processing power and memory available on the handheld glucose meter 10 can be streamlined, thereby reducing the cost of the handheld glucose meter 10.

Upon determining a blood glucose measurement at 71, the blood glucose measurement is first tagged at 72 with identifying information. Identifying information may include but is not limited to a name of the patient to which the measurement pertains to, a timestamp for when the measurement was taken, a serial number for the handheld glucose meter 10 and other information pertaining to the test strip. Each blood glucose measurement may be tagged with a unique sequence number assigned by the handheld glucose meter 10. In one embodiment, a counter is incremented each time a glucose measurement is taken and the value of the counter is assigned to the blood glucose measurement. The sequence number may be used to retrieve missing data from the handheld glucose meter 10 as is further described below. Once tagged, the blood glucose measurement is stored at 73 in a memory of the handheld glucose meter 10 and is displayed to the user at 74 on the display 11 of the handheld glucose meter 10.

Next, the handheld glucose meter 10 determines at 75 whether it is paired via a wireless data link with another device, such as mobile phone 18. The current blood glucose measurement is transmitted at 76 to the mobile phone 18 when the handheld glucose meter 10 is paired with the mobile phone 18. In one embodiment, the blood glucose measurement is transmitted automatically and without user intervention. In another embodiment, the blood glucose measurement is transmitted automatically in response to the user navigating away from the measurement result screen, for example by depressing the back button 15 on the handheld glucose meter 10. It is envisioned that the mobile phone 18 and/or the diabetes management application 16 is authenticated with the handheld glucose meter 10 during the pairing process.

In addition to transmitting the blood glucose measurement, the handheld glucose meter 10 can synchronize its time with the mobile phone 18. During initial setup or thereafter, the handheld glucose meter 10 may be configured by the user, using either the handheld glucose meter 10 or the mobile phone 18, to synchronize its clock with the mobile phone 18. By enabling this time synchronization feature, the user is designating the mobile phone 18 as the master device. Current time on the mobile phone 18 is transmitted to the handheld glucose meter 10 during each data exchange. Because a user is interacting frequently with their mobile phone 18, the time reported by the mobile phone 18 is likely to be accurate. The handheld glucose meter 10 will compare the current time on the mobile phone 18 to the current time maintained by the handheld glucose meter 10 as indicated at 77. If the time synchronization feature has been enabled by the user and the difference between the two clocks exceeds a variance (e.g., 2 minutes), the handheld glucose meter 10 will set its clock to the current time of the mobile phone 18 as indicated at 78. Conversely, the handheld glucose meter 10 may retain its current time if time synchronization feature has not been enabled or the difference between the two clocks is less than the variance threshold. In an alternative embodiment, the handheld glucose meter 10 will set its clock to the current time of the mobile phone 18 if the difference between the two clocks is less than the variance threshold and the time synchronization feature is enabled. It is envisioned that other parameters, such as date/time format, target glucose ranges, hypo waning levels, etc., can also be synchronized between the two devices.

During each data exchange, the handheld glucose meter 10 may also receive a request for missing glucose measurements at 79 from the diabetes management application 16. In one embodiment, the request identifies any missing glucose measurement by its sequence number. In response to receiving a request, the handheld glucose meter 10 transmits the missing glucose measures at 80 to the diabetes management application 16. It is to be understood that only the relevant steps are discussed in relation to FIG. 7 but that other software-implemented instructions may be needed to transmit data from the handheld glucose meter 10. In an exemplary embodiment, the method described above is implemented by a user interface module residing on the handheld glucose meter 10.

Figure 8:
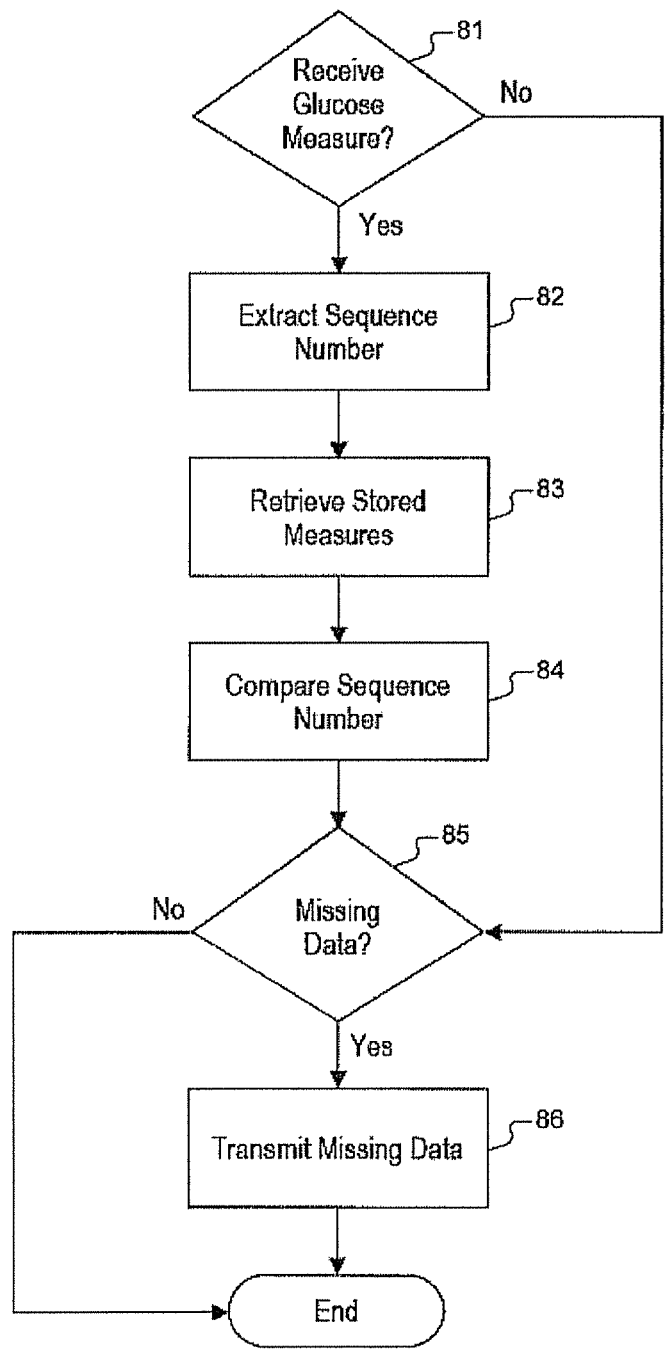
FIG. 8 is a flow diagram illustrating an example technique for processing glucose measurements received by a diabetes management application.

FIG. 8 depicts an example method for processing glucose measurements received by the diabetes management application 16 residing on the mobile phone 18. In this example embodiment, glucose measurements are transmitted individually to the diabetes management application 16 as described in relation to FIG. 7. It is envisioned that other techniques for transmitting the glucose measurement to the diabetes management application 16 are contemplated by this disclosure.

Upon receiving a glucose measurement at 81, a sequence number associated with the glucose measurement is first determined by the diabetes management application 16. A unique sequence number is assigned by the handheld glucose meter 10 to each glucose measurement as described above. Thus, the sequence number associated with the glucose measurement can be extracted at 82 from the data packet or message received from the handheld glucose meter 10. In some embodiments, a series of glucose measurements previously received from the handheld glucose meter 10, along with their associated sequence numbers, may be stored in a memory device and thus accessible to the diabetes management application 16. In other embodiments, only the most recently received glucose measurement and its sequence number is stored by the diabetes management application 16. In either case, the stored glucose measurement(s) along with associated sequence number(s) are retrieved from memory at 83.

A comparison is made at 84 between the sequence number extracted from the present glucose measurement and the sequence numbers of the stored glucose measurements. A request for missing glucose measurements is transmitted by the diabetes management application 16 to the handheld glucose meter 10 when an omission in the sequence is detected at 85. For example, a request for missing glucose measurements is transmitted at 86 when the extracted sequence number is 74 and the highest stored sequence number is either 71 or 72. Conversely, a request is not transmitted when the extracted sequence number is 74 and the highest stored sequence number is 73. Because this comparison is made for each glucose measurement received by the diabetes management application 16, a comparison of the extracted sequence number only needs to be made to the highest stored sequence number. In other embodiments, the diabetes management application 16 may analyze the series of glucose measurements for omitted measures and send a request for each glucose measurement missing from the series of glucose measurements.

Even when a glucose measurement is not received, the diabetes management application 16 can check for omitted glucose measurements as indicated at 81. As noted above, the diabetes management application 16 can analyze the series of glucose measurements for omitted measurements and send a request at 86 for each glucose measurement missing from the series of glucose measurements. It is to be understood that only the relevant steps are discussed in relation to FIG. 8 but that other software-implemented instructions may be performed by the diabetes management application 16.

In an example embodiment, the result screens 55, 55', 55" or 57 and the logbook screen 59 may be displayed on the mobile phone 18. After the diabetes management application 16 receives a current blood glucose measurement at 81, the diabetes management application 16 may display the result screen 55 on a display of the mobile phone 18. In response to receiving a selection of the indicium 58, the diabetes management application 16 may display the logbook screen 59 on the display of the mobile phone 18. If the mobile phone 18 includes a touchscreen display, then the indicium 58 may be selected via the touchscreen display.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for displaying glucose measurements of a person on a handheld glucose meter, the method comprising:
   determining, by the handheld glucose meter, a current blood glucose measurement for a person from a test strip inserted into a port of the handheld glucose meter, the test strip having a reaction site for receiving a sample of fluid from the person;
   displaying, by the handheld glucose meter, the current glucose measurement on a result screen of the handheld glucose meter immediately following the measurement of the current glucose measurement by the handheld glucose meter;
   providing, by the handheld glucose meter, an indicium of a logbook screen on the result screen concurrently with the display of the current glucose measurement on the result screen; and
   displaying, by the handheld glucose meter, the logbook screen in response to a single user input received by the handheld glucose meter, where the logbook screen displays the current glucose measurement along with at least two preceding glucose measurements of the person.

2. The method of claim 1, wherein the result screen only displays data associated with the current glucose measurement of the person.

3. The method of claim 1, wherein the result screen only displays data associated with the current glucose measurement and a single preceding glucose measurement of the person.

4. The method of claim 1, wherein the indicium of the logbook screen comprises an icon.

5. The method of claim 1, further comprising displaying a single preceding glucose measurement for the person on the result screen concurrently with the display of the current glucose measurement on the result screen.

6. The method of claim 5, wherein the indicium for the logbook screen comprises the single preceding glucose measurement for the person being displayed on the result screen.

7. The method of claim 6, further comprising receiving a selection of the single preceding glucose measurement as the user input for displaying the logbook screen.

8. The method of claim 1, further comprising receiving a selection of the indicium of the logbook screen as the user input for displaying the logbook screen.

9. The method of claim 1, further comprising highlighting the current glucose measurement on the logbook screen.

10. A handheld glucose meter comprising:
    a display;
    a port configured to receive a test strip having a reaction site for receiving a sample of blood from a patient;
    a glucose measurement module that operates to determine a current blood glucose measurement for a patient from a test strip inserted into the port of the handheld glucose meter; and
    a user interface module in data communication with the glucose measurement module and the display, the user interface module operates to
        display the current glucose measurement on a result screen of the display in response to the measurement of the current glucose measurement by the glucose measurement module;
        provide, on the display, an indicium of a logbook screen on the result screen concurrently with the display of the current glucose measurement on the result screen;
        receive a single user input to display the logbook screen while the current glucose measurement is displayed on the result screen; and
        display the logbook screen in response to the single user input received by the handheld glucose meter, where the logbook screen displays the current glucose measurement along with at least two preceding glucose measurements of the patient.

11. The handheld glucose meter of claim 10, wherein the result screen only displays data corresponding with the current blood glucose measurement of the patient.

12. The handheld glucose meter of claim 10, wherein the result screen only displays data corresponding with the current blood glucose measurement and a single preceding blood glucose measurement of the patient.

13. The handheld glucose meter of claim 10, wherein the indicium of the logbook screen comprises a user-selectable icon.

14. The handheld glucose meter of claim 10, wherein the user interface module further operates to display a single preceding glucose measurement for the patient on the result screen concurrently with the display of the current glucose measurement on the result screen.

15. The handheld glucose meter of claim 14, wherein the indicium for the logbook screen comprises the single preceding glucose measurement being displayed on the result screen.

16. The handheld glucose meter of claim 15, wherein the user interface module operates to receive a selection of the single preceding glucose measurement on the result screen as the user input to display the logbook screen.

17. The handheld glucose meter of claim 10, wherein the user interface module operates to receive a selection of the indicium of the logbook screen on the result screen as the user input to display the logbook screen.

18. The handheld glucose meter of claim 10, wherein the user interface module further operates to highlight the current glucose measurement of the patient on the logbook screen.

19. A method for displaying blood glucose measurements of a patient on a handheld blood glucose meter, the method comprising:
  determining, by the handheld blood glucose meter, a current blood glucose measurement for the patient from a test strip inserted into a port of the handheld blood glucose meter, the test strip having a reaction site for receiving a sample of blood from the patient;
  displaying, by the handheld blood glucose meter, the current blood glucose measurement on a result screen of the handheld blood glucose meter in response to the measurement of the current blood glucose measurement by the handheld blood glucose meter;
  displaying, by the handheld blood glucose meter, a single previous blood glucose measurement of the patient on the result screen concurrently with the display of the current blood glucose measurement on the result screen;
  receiving, by the handheld blood glucose meter, a selection of the single previous blood glucose measurement being displayed on the result screen; and
  displaying, by the handheld blood glucose meter, a logbook screen in response to the selection received by the handheld blood glucose meter, where the logbook screen displays the current blood glucose measurement along with at least two previous glucose measurements of the patient.

20. The method of claim 19, wherein the result screen only displays data corresponding with the current blood glucose measurement and the single previous blood glucose measurement of the patient.

* * * * *